(12) United States Patent
Hartman et al.

(10) Patent No.: US 10,548,798 B2
(45) Date of Patent: Feb. 4, 2020

(54) PHYSIOTHERAPY APPARATUS

(75) Inventors: Johannes Bastiaan Hartman, Delft (NL); Arie Van Baren, Rotterdam (NL)

(73) Assignee: ENRAF-NONIUS B.V., Rotterdam (NL)

(*) Notice: Subject to any disclaimer, the term of this patent is extended or adjusted under 35 U.S.C. 154(b) by 999 days.

(21) Appl. No.: 13/637,982

(22) PCT Filed: Mar. 29, 2011

(86) PCT No.: PCT/EP2011/054856
§ 371 (c)(1),
(2), (4) Date: Nov. 8, 2012

(87) PCT Pub. No.: WO2011/120985
PCT Pub. Date: Oct. 6, 2011

(65) Prior Publication Data
US 2013/0085531 A1 Apr. 4, 2013

(30) Foreign Application Priority Data

Mar. 30, 2010 (WO) ................ PCT/EP2010/054160

(51) Int. Cl.
*A61H 1/00* (2006.01)
*A61H 1/02* (2006.01)
*A61F 5/01* (2006.01)

(52) U.S. Cl.
CPC ............ *A61H 1/0296* (2013.01); *A61F 5/01* (2013.01); *A61H 1/00* (2013.01); *A61H 1/02* (2013.01);
(Continued)

(58) Field of Classification Search
CPC .......... A61H 1/00; A61H 1/003; A61H 1/005; A61H 1/006; A61H 1/008; A61H 1/02;
(Continued)

(56) References Cited

U.S. PATENT DOCUMENTS 4,893,808 A * 1/1990 McIntyre ............. A63B 23/025
482/10
4,936,299 A * 6/1990 Erlandson .......... A63B 69/0053
482/9

(Continued)

FOREIGN PATENT DOCUMENTS

DE 10351455 6/2005
DE 102004020817 12/2005
(Continued)

OTHER PUBLICATIONS

Russian Office Action from corresponding Russian Application No. 2012143848/14(070405), dated Mar. 29, 2011, dated Jul. 14, 2015.
(Continued)

*Primary Examiner* — Tu A Vo
(74) *Attorney, Agent, or Firm* — Steven M. Koehler; Westman, Champlin & Koehler, P.A.

(57) ABSTRACT

An apparatus for treating a body part of a patient is provided. The apparatus comprises a support for at least partially supporting and holding the body part and a manipulator connected to the support for supporting and maneuvering the support. The manipulator includes a parallel linkage device including a plurality of hingedly interconnected linear actuators. The parallel linkage device includes at least one hinge including a, preferably resilient, tendon joint. Further, a method, a storage medium and a piece of headgear are provided.

20 Claims, 8 Drawing Sheets

(52) U.S. Cl.
CPC ......... *A61H 1/0237* (2013.01); *A61H 1/0274* (2013.01); *A61H 2001/0207* (2013.01); *A61H 2201/1238* (2013.01); *A61H 2201/1246* (2013.01); *A61H 2201/1607* (2013.01); *A61H 2201/1611* (2013.01); *A61H 2201/1616* (2013.01); *A61H 2201/5007* (2013.01); *A61H 2201/5038* (2013.01); *A61H 2201/5058* (2013.01); *A61H 2201/5064* (2013.01); *A61H 2201/5079* (2013.01); *A61H 2201/5084* (2013.01); *A61H 2201/5097* (2013.01); *A61H 2203/0456* (2013.01)

(58) Field of Classification Search
CPC .... A61H 2001/0203; A61H 2001/0207; A61H 1/0214; A61H 1/0292; A61H 1/0296; A61H 2201/01; A61H 2201/0142; A61H 2201/0138; A61H 2201/12; A61H 2201/1207; A61H 2201/1215; A61H 2201/123; A61H 2201/1238; A61H 2201/1604; A61H 2201/1609; A61H 2201/165; A61H 2201/1657; A61H 2201/1659; A61H 2201/1664; A61H 2201/1666; A61H 2201/1671; A61H 2201/1673; A61H 2201/1676; A61H 2201/50; A61H 2201/5058; A61H 2201/5064; A61H 2201/5097; A61H 2201/5071; A61H 2201/5092; A61H 2201/5076; A61H 2205/02; A61H 2203/0443; A61H 2203/0456
USPC ............................................ 606/245; 601/39
See application file for complete search history.

(56) References Cited

U.S. PATENT DOCUMENTS

| | | | | |
|---|---|---|---|---|
| 5,425,378 A | | 6/1995 | Swezey et al. | |
| 5,466,213 A | * | 11/1995 | Hogan | A61H 1/02 |
| | | | | 482/4 |
| 5,575,597 A | * | 11/1996 | Bailey | B23Q 1/5462 |
| | | | | 408/234 |
| 5,645,077 A | | 7/1997 | Foxlin | |
| 5,987,726 A | * | 11/1999 | Akeel | B23P 19/105 |
| | | | | 29/407.08 |
| 6,120,453 A | | 9/2000 | Sharp | |
| 6,162,189 A | * | 12/2000 | Girone | A61B 5/1036 |
| | | | | 482/79 |
| 6,551,214 B1 | * | 4/2003 | Taimela | A61H 1/0296 |
| | | | | 482/10 |
| 6,581,437 B2 | * | 6/2003 | Chrystall | A43D 999/00 |
| | | | | 73/7 |
| 6,695,796 B1 | * | 2/2004 | Solmor | A61G 13/121 |
| | | | | 128/845 |
| 7,395,181 B2 | * | 7/2008 | Foxlin | G01C 21/165 |
| | | | | 128/897 |
| 2004/0220500 A1 | * | 11/2004 | Dahl | A61B 5/1121 |
| | | | | 601/5 |
| 2004/0254771 A1 | * | 12/2004 | Riener | G09B 23/32 |
| | | | | 703/7 |
| 2006/0079817 A1 | * | 4/2006 | Dewald | A61H 1/02 |
| | | | | 601/5 |
| 2006/0277074 A1 | * | 12/2006 | Einav | G16H 10/60 |
| | | | | 705/3 |
| 2006/0293617 A1 | * | 12/2006 | Einav | A61H 1/0274 |
| | | | | 601/33 |
| 2007/0221480 A1 | * | 9/2007 | Lynch | B65G 27/00 |
| | | | | 198/752.1 |
| 2007/0282228 A1 | * | 12/2007 | Einav | A61B 5/7475 |
| | | | | 601/33 |
| 2007/0284502 A1 | * | 12/2007 | Hsin | G02B 7/005 |
| | | | | 248/495 |
| 2007/0299371 A1 | * | 12/2007 | Einav | G06F 19/00 |
| | | | | 601/5 |
| 2008/0104763 A1 | * | 5/2008 | Brown | A61G 7/0573 |
| | | | | 5/636 |
| 2009/0098519 A1 | * | 4/2009 | Byerly | G09B 23/28 |
| | | | | 434/247 |
| 2009/0105714 A1 | | 4/2009 | Kozak | |
| 2009/0112262 A1 | | 4/2009 | Pool | |
| 2009/0272385 A1 | * | 11/2009 | River | A61H 1/0296 |
| | | | | 128/845 |
| 2009/0281465 A1 | * | 11/2009 | Fu | A61H 1/0274 |
| | | | | 601/5 |
| 2012/0143104 A1 | * | 6/2012 | Tee | A61H 1/02 |
| | | | | 601/23 |

FOREIGN PATENT DOCUMENTS

| | | |
|---|---|---|
| DE | 202008015138 | 4/2009 |
| EP | 1880702 | 1/2008 |
| WO | 9953838 A1 | 10/1999 |
| WO | 0015114 | 3/2000 |
| WO | 0071026 | 11/2000 |
| WO | 2006039403 | 4/2006 |
| WO | 2008059497 | 5/2008 |

OTHER PUBLICATIONS

International Search Report, dated Nov. 10, 2011 in connection with International Patent Application No. PCT/EP2011/054856.
Machine translation of DE 102004020817.
Machine translation of DE 10351455.
Machine translation of DE 202008015138.
Machine translation of WO 0015114.
International Search Report, dated Dec. 2, 2010 in connection with International Patent Application No. PCT/EP2010/054160.
European Search Report dated Jun. 28, 2017 for corresponding European patent application No. 16188991.0.
Office Action for Canadian Patent Application No. 2828900, dated Apr. 3, 2017, 4 pages.

* cited by examiner

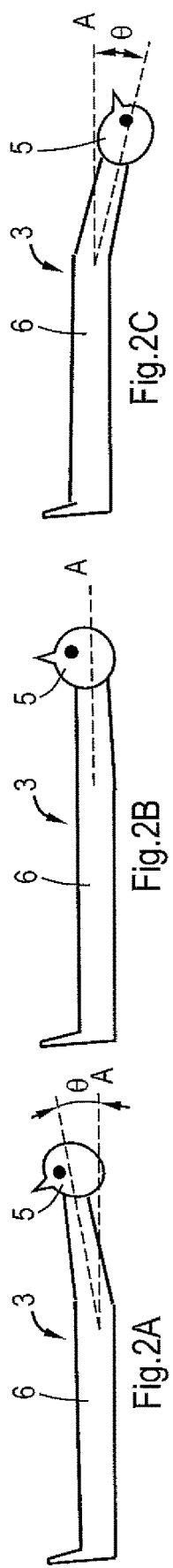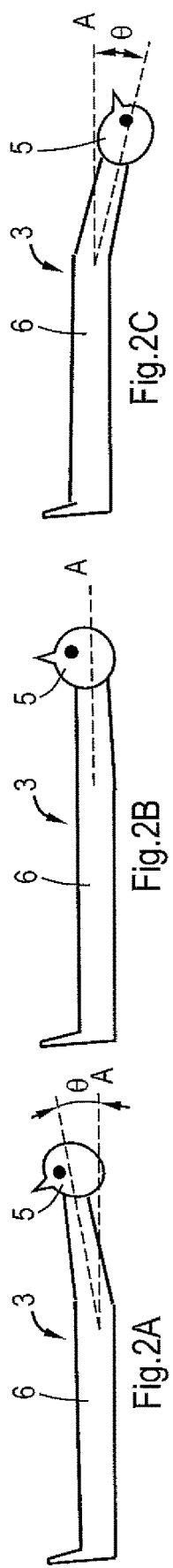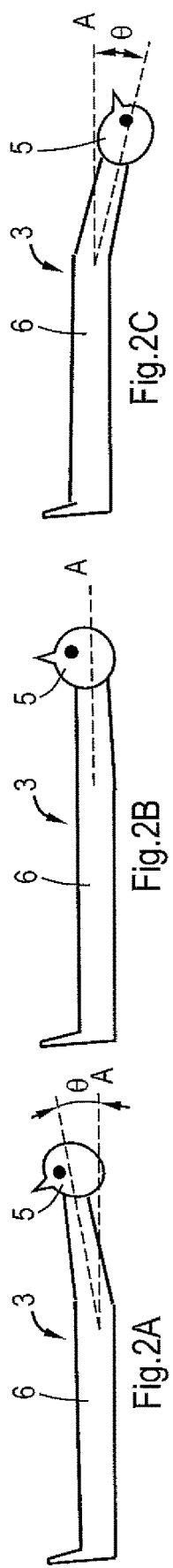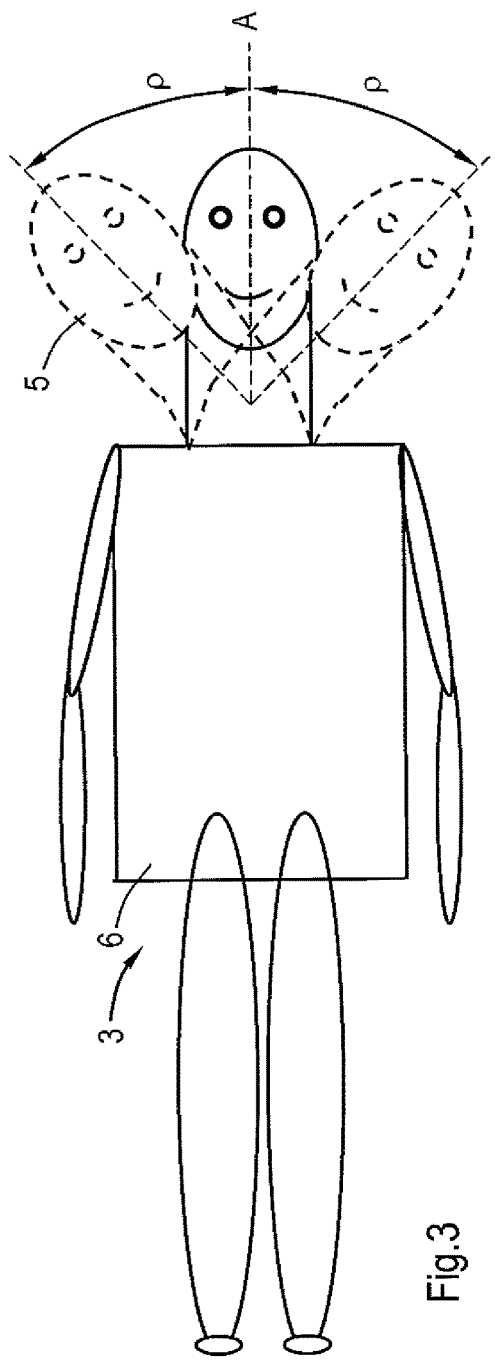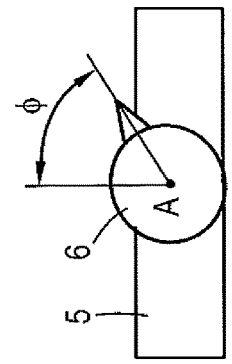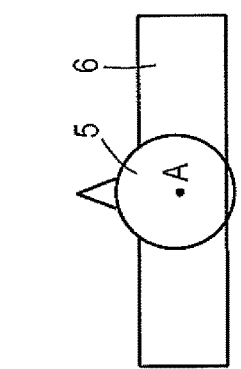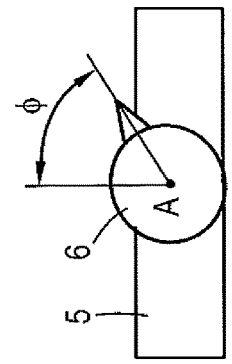

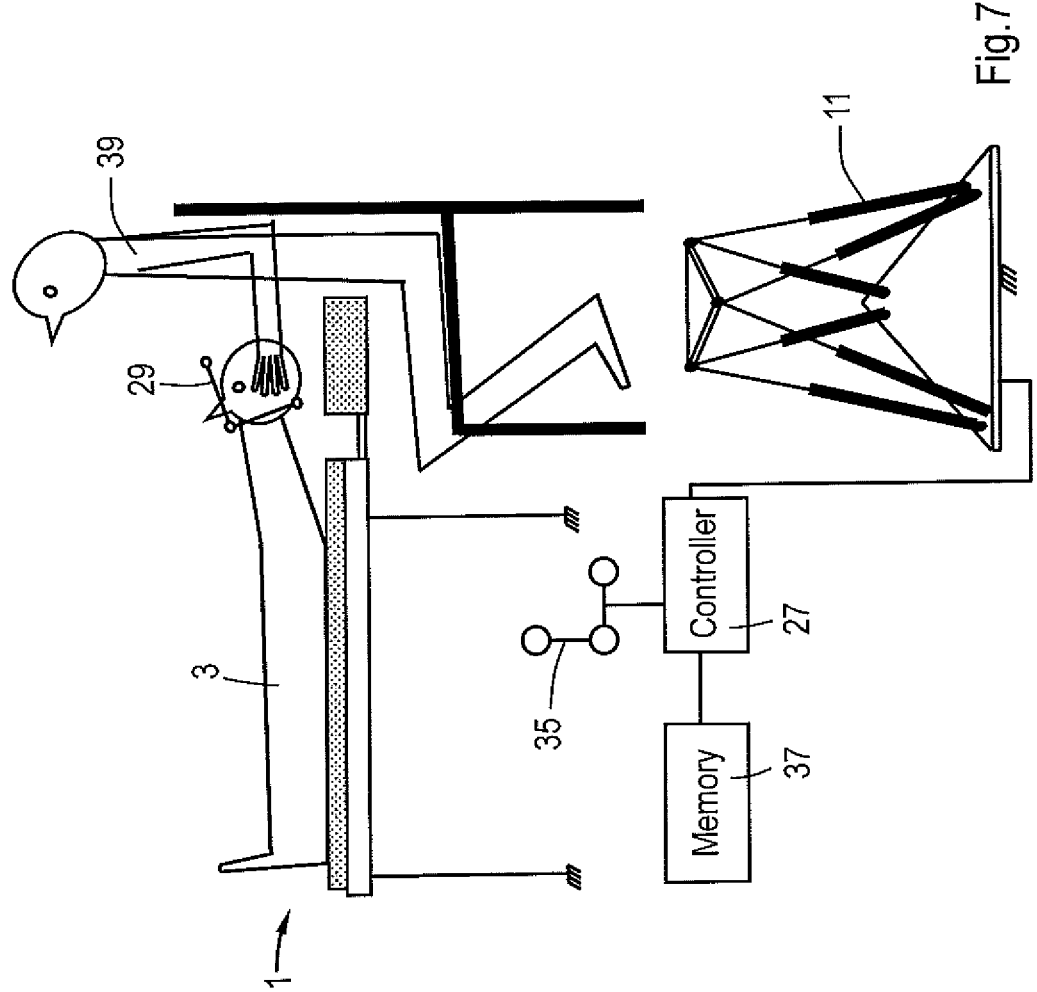

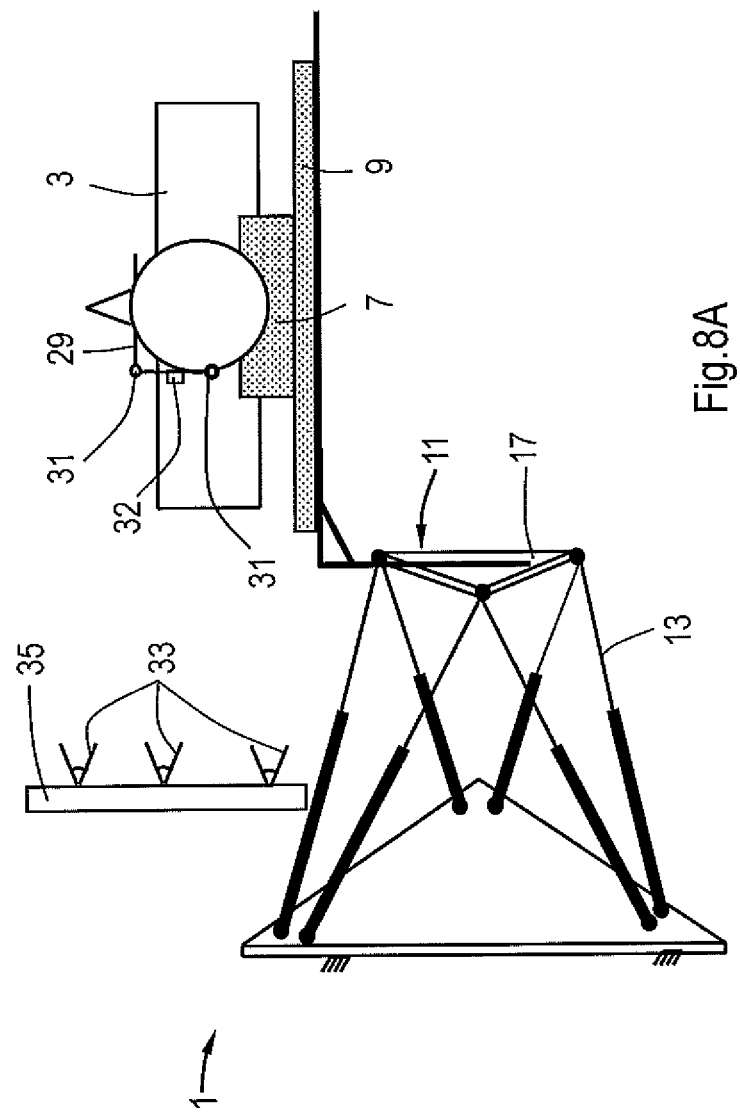

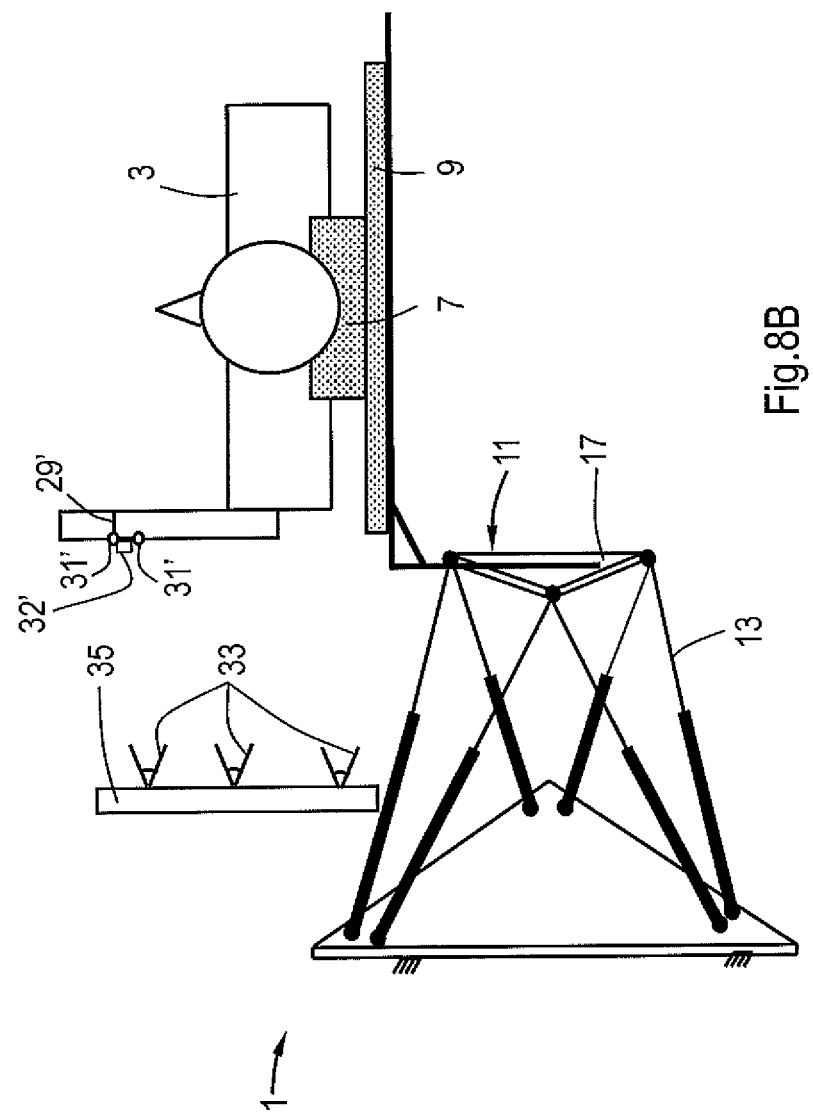

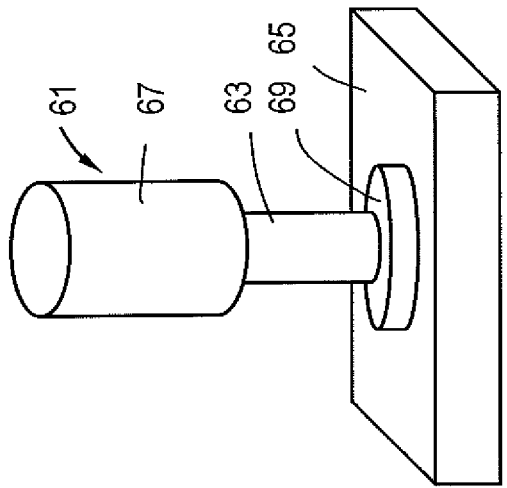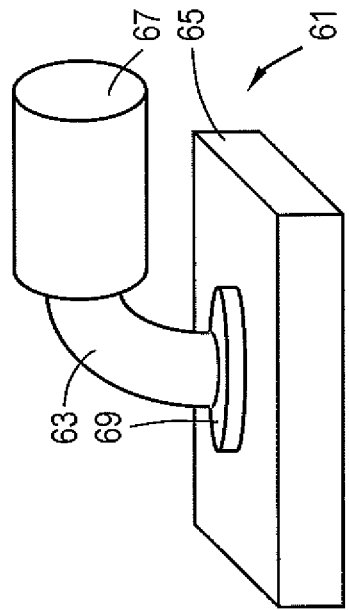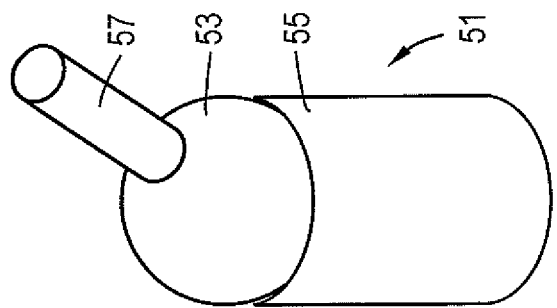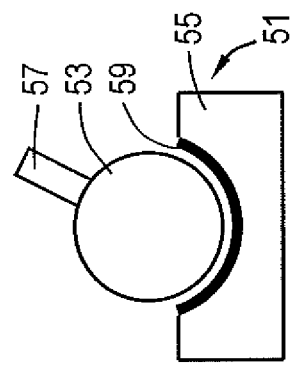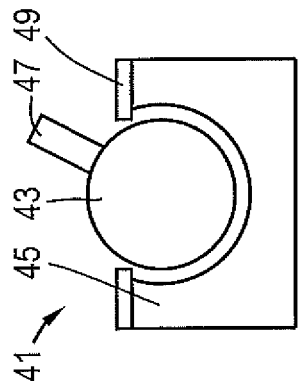

PHYSIOTHERAPY APPARATUS

PRIORITY CLAIM(S) AND/OR CROSS REFERENCE(S) TO RELATED APPLICATION(S)

This application is a national stage application under 35 U.S.C. § 371 of PCT/EP 2011/054856, filed Mar. 29, 2011, published as WO 2011/120985 A2 on Oct. 6, 2011, and claiming priority to International Application PCT/EP 2010/054160 filed Mar. 30, 2010, which both application and publications are incorporated herein by reference and made a part hereof in its, entirety, and the benefit of priority of which is claimed herein.

TECHNICAL FIELD

The present disclosure relates to the field of physiotherapeutic apparatus, in particular apparatus for dynamic physiotherapy, more in particular apparatus for dynamic physiotherapy of the head, neck and/or shoulders. In another aspect the present disclosure relates to determination of the position and/or displacement of a body part.

BACKGROUND

In physiotherapy, in particular orthopaedic physiotherapy, one may distinguish between active therapies and passive therapies. In active therapies, predetermined movements are performed by the patient in exercise and training sessions. In passive, or administered therapies, a patient is treated by manipulating one or more body parts. Two different types of administered treatment are distinguished: static therapies and dynamic therapies.

In a static therapy, a patients body part is brought in a predetermined position and a predetermined force is applied to the body part for a predetermined time to maintain the body part in that position. Such static treatment facilitates the use of apparatus to provide a controllable predetermined force (strength and direction) for a desired duration. E.g. various traction devices are available which may comprise a simple pulley. A more complex robotic traction device is disclosed in DE 20 2008 015 138.

In a dynamic therapy, the treated body part is maneuvered, along a predetermined trajectory, usually with predetermined velocity and/or force. This requires delicate control of the movement so as not to inflict pain or harm to the patient. Maneuvering a body part means moving, continuously or intermittently, the body part by external forces e.g. by another person such as the therapist.

For administering a dynamic therapy to the head and neck of a patient according to different methods, WO 2008/059497 discloses an apparatus for treating a patient body or an organ thereof, especially his/her head and neck, by controllably maneuvering said treated organ, comprising; a cradle adapted for holding said treated organ stably and comfortably; and a maneuverable platform upon which said cradle rests, comprising maneuvering means adapted for rotating the platform in the Sagittal, Coronal, Horizontal planes or in any combination of the planes thereof for a predetermined duration; wherein said maneuver of said organ is characterized by parameters selected from a set of Allowed Movements as defined in the document, where duration of motion in all cases is up to about 90 sec.

Due to the structure of the joint to be treated and/or due to patient limitations (flexibility, afflictions, pain, etc.), a therapeutic maneuvering trajectory may be complex. This is in particular the case for movement of the head, neck and shoulders which includes varying and moving centres of rotation and/or relative translations. To allow treatment of a neck the apparatus disclosed in WO 2008/059497 relies on serial linkage of motors as well as on biofeedback (muscle tension etc.) Thus the apparatus suffers from large size and complexity, as well as from accumulation of errors in position and orientation from one motor to the next, reducing accuracy of the position and orientation of the cradle. Such apparatus further tends to be expensive and may be intimidating to patients, preventing their relaxation during treatment which reduces effectiveness of the treatment.

It is an object of the present disclosure to provide an improved apparatus for providing dynamic administered physiotherapeutic treatment. A further object is to provide an apparatus for improving determination of a spatial position, orientation of a body part and determination of a displacement.

SUMMARY

In a first aspect, an apparatus is provided which is configured for treating a body part of a patient. The apparatus comprises a support for at least partially supporting and holding the body part and a manipulator connected to the support for supporting and maneuvering the support.

The manipulator comprises a parallel linkage device, such as a double tripod, a pentapod or a Stewart platform or a hexapod, which provides a better accuracy and a much higher stiffness for a given structural mass than a serial linkage device, and conversely, which can have a reduced mass for a given desired stiffness. Reduced mass results in reduced power consumption and increased accuracy in manipulation and maneuvering. A manipulator providing controlled positioning of the support in six degrees of freedom (three mutually perpendicular directions of translation (X, Y, Z) and three degrees of rotation about the directions of translation (roll, pitch, yaw)) allows performing complex motions and trajectories with the support. A solid angle spanned by plane angles ($\theta$, $\phi$, $\rho$) in mutually perpendicular directions of approx. (45°, 45°, 45°) allows access to the range of motion of the head of a normal, healthy and pain-free human of approx. 90 years and allows preventing asymmetric treatment. The translational degrees of freedom allow accounting for the varying and moving centres of rotation and/or relative translations in a neck movement.

In a preferred apparatus (the parallel linkage device of) the manipulator comprises a Stewart-platform having a six linear actuators connected to two support members via hinges. A Stewart platform may take up a small volume relative to its achievable range of motion. Further, Stewart platforms are generally reliable and provide little risk of singularities, i.e. points in which the position, motion and or direction of the two support members with respect to each other are not uniquely defined or where a degree of motion has become inaccessible or "frozen out", e.g. in a condition known as gimbal lock. A Stewart platform may even be designed to be substantially free of singularities. Thus, safety of the apparatus is increased.

One or more hinges, advantageously all hinges of a parallel linkage device may comprise magnetic ball joints. This reduces the number of parts and reduces friction and maintenance compared to biaxial universal joints (cardanic joints). A magnetic ball joint also obviates a housing to retain the ball of a non-magnetic ball joint, again reducing friction and the number of parts. Further, the range of motion of the joint and thus of the manipulator is increased, facilitating achieving the solid angle spanned by plane angles (θ, φ, ρ) in mutually perpendicular directions of approx. (45°, 45°, 45°) described above. A magnetic ball joint may be enveloped at least partly by a flexible tube to assist preventing dislocation of the joint.

One or more hinges, advantageously all hinges of a parallel linkage device may comprise a tendon joint. Within this text, a tendon joint is any type of joint wherein two objects are movably interconnected by a third member, the tendon, which is flexible at least in two perpendicular directions such as a rod or tube of plastic, natural and/or synthetic rubber, a helical or other type spring, a piece of cable, e.g. steel cable, etc. Generally the flexibility of a tendon joint is such that in relaxed and unloaded state the tendon extends substantially straight in stick-, bar- or rod-like fashion without hanging down by its own weight in horizontal position. Tendon joints may allow a range of motion over a vast solid angle, facilitating achieving the solid angle described above. The range of motion of a tendon joint may be determined by selecting material, diameter, length and/or shape of the joint, e.g. substantially cylindrical to substantially hour-glass-shaped rod. A tendon joint provides a direct link between the hinged parts connected by the joint, preventing dislocation of the joint. Rubber universal joints and helical springs with diverse specifications are commercially available, generally at significantly lower cost than a cardanic joint or a (magnetic) ball joint.

Magnetic ball joints and in particular tendon joints require little to no housing for attachment and thus may occupy little volume. Thus, hinges of a manipulator may be arranged close together. This increases freedom of movement of the manipulator.

It has been found that a parallel linkage device, in particular a Stewart platform, comprising a plurality of hingedly interconnected linear actuators with cardanic universal joints or non-magnetic ball joints generally has a range of motion in a solid angle which is restricted to approx. 30 degrees per direction of rotation (roll, pitch, yaw) and which may restrict the translational range of motion. In order to reduce chances of singularities of such device, in particular in the case of Stewart platforms, one or more cardanic universal joints may be fixed to a base or platform. However, this reduces the range of motion of the device and may affect symmetry of the remaining range of motion. Using magnetic ball joints and/or tendon joints the rotational range of motion (roll, pitch, yaw) of the device, in particular a Stewart platform, as well as the translational range of motion may be significantly increased for equal actuators. The improved therapeutic apparatus disclosed in this text exemplifies that.

To utilise one or more of the above described benefits in an existing Stewart platform, or any parallel linkage device, it may be improved by modifying it by replacing one or more of its existing hinges with tendon joints.

A resilient hinge, in particular a resilient tendon joint provides a restoring force to the manipulator assisting restoring a default position. It further can function as a shock absorber and it can reduce jerk of the manipulator (jerk j being the derivative with respect to time of acceleration a or, equivalently, second derivative of velocity v and third derivative of position s: $j=da/dt=d^2v/dt^2=d^3s/dt^3$). Thus smoother motion of the object supported by the manipulator, here the support, is provided and thus smoother motion of the body part. Such benefit is independent of the translational or rotational freedom and/or range of motion of the manipulator and thus of an apparatus comprising the manipulator.

The advantages of a tendon joint, in particular a resilient tendon joint, for a parallel linkage device with linear actuators may benefit other parallel linkage devices and uses thereof.

Rubber tendon joints with diverse specifications are commercially available, generally at significantly lower cost than a cardanic joint or a (magnetic) ball joint.

In the case of the present apparatus comprising resilient tendon joints, movements of (the body part of) the patient may be accommodated somewhat, defined by the resiliency of the joints. A patient may thus resist to a certain extent an intended amplitude of a movement of the support. Comfort and (sense of) security for patients are therefore significantly increased.

At least one of the said linear actuators may comprise at least one spindle actuator. A spindle actuator may be lightweight and provide a large actuator stroke compared to a hydraulic or pneumatic cylinder of equal strength and equal length at minimum extension. A spindle further is self-braking, thus increasing safety of the apparatus. Further, a spindle actuator may have little diameter with respect to its strength, compared to other types of actuators, allowing close arrangement of the actuators which benefits the freedom of movement of the manipulator.

The apparatus may comprise a servo motor and/or stepper motor for operating one or more of the said linear actuators accurately and reliably. Servo motors and stepper motors are generally reliable for determining both absolute and relative adjustments.

A stepper or servo motor in combination with a spindle actuator allows providing constant accuracy throughout the full stroke of the actuator, as well as operation at high speed. This enables executing movements for complex trajectories. By selecting the thread pitch of the spindle and the step-size of the motor the positional accuracy of the actuator, and here thus the accuracy of the position and orientation of the apparatus.

For improving reliable definition of movements of the body part relative to a second body part the apparatus may further comprise a second support for supporting a second support, such as rest, a chair, a couch or a bed, for stationary supporting the further body part.

A physiotherapy apparatus may comprise a first portion and a second portion, the first portion comprising a plurality of sources for emitting a signal and the second portion comprising a plurality of detectors for detecting at least a portion of the signal. Each signal emitted from a source and detected by a detector has a signal travelling time between the respective source and detector. The apparatus comprising a controller configured to determine a plurality of signal travelling times between at least some of the sources and at least some of the detectors allows to determine, advantageously be the controller, on the basis of the determined plural signal travelling times, the spatial position and orientation of the first and second portions relative to each other.

The first portion may comprise the support and the second apparatus portion may be the second support or another object. Advantageously, the first apparatus portion comprises an object which is easily connectable to, e.g. wearable on, the body part, such as a helmet, a spectacles-frame, a head band, a wrist strap, etc. This allows determination of the position and movement of the body part independent of the position of the support and/or the manipulator relative to the body part, e.g. during maneuvering of the body part by a therapist.

Advantageously, the signal comprises an ultrasound signal, this reduces electromagnetic noise and it is not noticeable by humans.

Further, the source may be configured for contemporary emitting a first signal and a second signal, the first signal being a relatively slow signal, advantageously an ultrasound signal and the second signal being a relatively fast signal, e.g. an electric, radiographic and/or optical signal. If the travelling time for the second signal is negligible compared to the first signal, the second signal may efficiently be used for triggering a measurement of the travelling time of the first signal. This facilitates the measurement and the collection of data.

To record at least part of a maneuvering sequence or a trajectory, the apparatus may be configured for storing a plurality of the determined spatial positions and orientations of the first and second portions relative to each other in a memory. Further, time stamps corresponding to at least some of the determined spatial positions and orientations may be stored for providing velocity and acceleration information.

The memory may be integrated in the apparatus, be removable and/or remote e.g. a disk, a solid data-recording device and/or a remote computer.

The apparatus may further comprise a controller configured to read at least part of the information stored in the memory; to define at least a first maneuvering sequence of the body part as a function of the information stored in the memory; and to control the apparatus to operate at least part of the manipulator, e.g. one or more actuators, to maneuver the support in such a way that the body part, when appropriately positioned on, and possibly held by, the support, is maneuvered according to at least the first maneuvering sequence.

This allows recreating a recorded trajectory, in particular a trajectory of the body part itself.

In a further aspect a method is provided, which is a method of determining a spatial position and an orientation of a first object relative to a second object, the first object comprising a plurality of ultrasound signal sources and the second object comprising a plurality of ultrasound signal detectors for detecting a signal of the signal sources. The method comprises the steps of emitting a signal from at least one signal source of the plurality of signal sources and detecting the signal with at least one detector of the plurality of signal detectors such that each signal emitted from one of the sources and detected by one of the detectors has a signal travelling time between the respective source and detector; determining the plurality of signal travelling times of a predetermined signal from one source to plural detectors and/or a predetermined signal from plural sources to one detector; determining, on the basis of the determined plural signal travelling times, at least one of the position of the one source relative to the plural detectors, and respectively, the position of the one detector relative to the plural sources; and repeating the method steps of emitting and detecting a signal, determining signal travelling times and determining relative positions, with different combinations of sources and detectors, and determining from the determined relative positions the spatial position and orientation of the first and second objects relative to each other.

With the method, the position and orientation of the first and second objects relative to each other is easily and reliably determined using triangulation with plural positions. A single source and three detectors, or three sources and a single detector, satisfies for determining the relative positions of two objects. Using three sources and three detectors the relative position and orientation of three dimensional objects may be uniquely defined with a minimum number of sources and detectors.

By repeating the method steps and storing the determined spatial positions and orientations of the first and second objects relative to each other in a memory a trajectory of the first and second objects relative to each other can be recorded. Further, time stamps corresponding to at least some of the determined spatial positions and orientations may be stored for providing velocity and acceleration information to the trajectory.

In case the first or second object is a rigid object at rest, e.g. a building structure such as a wall, that object may suitably serve as a reference.

The above-described aspects will hereafter be further explained with further details and benefits with reference to the drawings showing embodiments of the invention by way of example.

BRIEF DESCRIPTION OF THE DRAWINGS

FIGS. 2A-4C illustrate basic movements of a human head;

FIGS. 6 and 7 illustrate use of the apparatus of FIG. 5;

FIG. 8A illustrates an alternative embodiment of an apparatus for treating a head of a patient;

FIG. 8B illustrates an alternative embodiment of an apparatus for treating a body part of a patient;

FIGS. 9-10B show different ball joints;

FIGS. 11A-14 show different tendon joints.

DETAILED DESCRIPTION OF EMBODIMENTS

Figure 1:
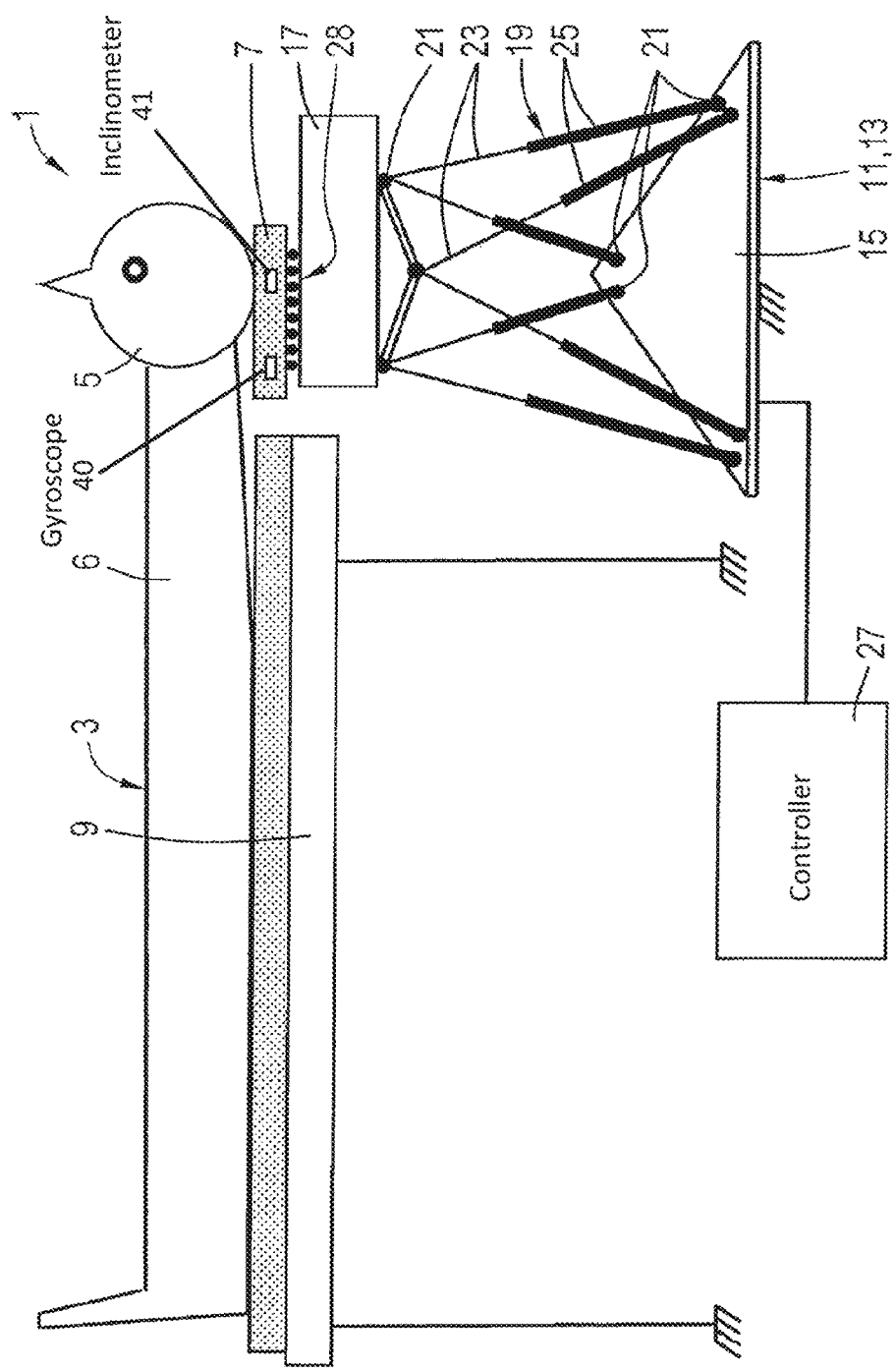
FIG. 1 illustrates an apparatus for treating a head of a patient.

It is noted that the drawings are schematic, not necessarily to scale and that details that are not required for understanding the present invention may have been omitted. The terms "upward", "downward", "below", "above", and the like relate to the embodiments as oriented in the drawings, unless otherwise specified. Further, elements that are at least substantially identical or that perform an at least substantially identical function are denoted by the same numeral, where useful individualised by an alphabetic suffix.

FIG. 1 shows an apparatus 1 which is configured for treating a patient 3 by controllably maneuvering at least a body part, here the head 5 with respect to the torso 6 of the patient 3. The apparatus 1 comprises a support 7 for supporting the head 5 and a second support 9 in the form of a bench for supporting the torso and limbs of the patient 3. The second support 9 may comprise plural portions which may be movable with respect to each other, e.g. for patient comfort (not shown). A manipulator 11 is connected to the support 7 for supporting and maneuvering the support 7. The support 7 may comprise a cushion, a cradle and/or means to provide and maintain a particular position of the head with respect to the support 7.

The shown manipulator 11 comprises a parallel linkage device 13, here in the form of a Stewart platform or hexapod 13 having a base 15, a platform 17 and six linear actuators 19, connected to the base 15 and platform 17 with hinges 21. Each linear actuator 19 comprises a threaded spindle 23 rotatably received in a threaded portion inside a tube 25. Other types of actuators e.g. hydraulic or pneumatic actuators, pulley actuators, gear racks or spindle actuators not having a tube, etc, are conceivable. However, a spindle actuator generally is preferable for, in comparison to other actuator types, being less expensive, requiring less maintenance, and being lighter-weight. Each actuator 19 is driven by a motor 20 (such as a servo motor or a stepper motor) to vary the length of the respective actuator 19. The combination of lengths of each actuator 19 determines the relative position and orientation of the base 15 and platform 17 of the Stewart platform 13. Since the support 7 is connected to (the platform 17 of) the manipulator 11 the relative position and orientation of the support 17 are determined by adjusting the actuators 19. A controller 27 is connected to the manipulator 11 to control the actuators 19 of the apparatus 1 to maneuver the support 7. Thus, the head 5, when appropriately positioned on or in the support 7 can be maneuvered.

Further, an optional bearing 28 is provided to allow movement of the support 7 with respect to the platform 17 to increase freedom of movement of the neck in one or more directions with respect to the platform 17. Movement in a particular direction may be determined with needle bearings and/or a guide, for movement in plural directions ball bearings may be used. A benefit is increased flexibility and comfort to the patient 3, however at the cost of reduced controllability of the position and/or trajectory of the head 5 with respect to the platform 17.

FIGS. 2A-2C, 3, and 4A-4C illustrate basic movements of the head 5 of the patient 3, the three substantially perpendicular movements of sagittal flexion about an angle $\theta$ determined in a sagittal plane (FIGS. 2A-2C), coronal tilt about an angle $\rho$ determined in a coronal plane (FIG. 3) and horizontal rotation about an angle $\phi$ determined in a transversal plane (FIGS. 4A-4C). The orientation ($\theta$, $\phi$, $\rho$) of the head is defined with respect to the anatomic longitudinal axis A. Since a human neck comprises seven vertebrae, only theoretically perfect horizontal rotation results in rotation about a fixed rotational axis, sagittal flexion and coronal tilt involve both rotation and translation of the centre of rotation. Combined movements in plural directions out of the planes are also possible so that the head 5 can move in a solid angle $\Omega$ generally spanned by the range of angles ($\theta$, $\phi$, $\rho$) achievable (not shown).

Similar considerations apply for other joints, which may achieve larger (e.g. shoulder) or smaller (e.g. knee) solid angles.

A primary object of physiotherapy is to achieve normal mobility (movement velocity and range) for the patient, or at least as close and as comfortable as possible for the particular patient.

The range of motion found for normal healthy people between 10 and 90 years is indicated in the following Table 1, indicating movement (see FIGS. 2A-4C; sagittal extension (not shown) is pushing the face forward with the head parallel to the torso, wherein the angle of the neck with respect to the torso is measured), maximum angle achieved by that movement and total range of motion in that movement.

TABLE 1

| Range of Motion | | |
|---|---|---|
| Movement | Max [°] | Total [°] |
| Sagittal flexion angle $\theta$ | 45-60 | 90-130 |
| Sagittal extension | 55-70 | |
| Coronal tilt angle $\rho$ | 45 | 90 |
| Horizontal rotation angle $\phi$ | 60-80 | 120-160 |

The range of motion tends to decrease with age for humans. Supple persons and younger persons may achieve the higher values listed, e.g. adolescents may achieve a range of flexion of approx. 130-135 degrees, with $\theta$ between approx. $-70°$ and $70°$, a range of tilt of approx. 90, with $\rho$ between $-45°$ and $45°$ and horizontal rotation in a range of approx. 160 degrees, with $\phi$ between $-80°$ and $80°$. To treat an elder patient the lower range of motion should preferably be available. To allow treatment of most patients, including accounting for differences in stature and afflictions, manipulation of a head up to a sagittal flexion angle $\theta$ of approx. $-70°$ (backward) and $70°$ (frontward), up to a coronal tilt angle $\rho$ of approx. $-50°$ (left) and $50°$ (right), and up to a horizontal rotation angle $\phi$ up to approx. $-45°$ (left) and $45°$ (right) may be provided, since a limitation in the horizontal rotation may easily be compensated by a patient by rotating the shoulders or part of the torso. A horizontal rotation angle $\phi$ up to approx. $-90°$ (left) and $90°$ (right) may be preferred to treat the neck itself without requiring shoulder or torso rotation.

A translational motion in the coronal direction of approx. 15-20 cm is desired for accounting for the curvature of the neck vertebrae and/or displacement of the cranium of average adults when treating coronal tilt. A similar translational motion is desired in the sagittal direction when treating flexion. Larger ranges of translational motion, e.g. 30 cm or up to 40 cm in at least the coronal direction are preferred to facilitate treatment of taller patients. Advantageously, the translational range of motion is substantially equal in two dimensions parallel to the coronal plane (e.g. horizontal), and it may be substantially equal in a third dimension, in a sagittal plane.

Thus, the manipulator 11 may maneuver the body part 5 in a volume spanned by the combination of translation and rotation range of motion. Whereas static physiotherapy generally concerns only maintaining relative positions and orientations of the treated body part, in dynamic physiotherapy therapeutic maneuvers are known for different afflictions. A maneuver may be effected in a desired duration corresponding to a particular motion velocity. A typical sequence of maneuvering steps for physiotherapeutic treatment of a head and neck is defined in Table 2, wherein each step may take from approx. 30 to approx. 90 seconds:

TABLE 2

| therapeutic manoeuvring sequence | | | |
|---|---|---|---|
| Step | Movement | Start Angle | End Angle |
| 1 | Sagittal flexion front | (0°, 0°, 0°) | (70°, 0°, 0°) |
| 2 | Sagittal return | (70°, 0°, 0°) | (0°, 0°, 0°) |
| 3 | Coronal tilt right | (0°, 0°, 0°) | (0°, 45°, 0°) |
| 4 | Coronal return right | (0°, 45°, 0°) | (0°, 0°, 0°) |
| 5 | Coronal tilt left | (0°, 0°, 0°) | (0°, −45°, 0°) |
| 6 | Coronal return left | (0°, −45°, 0°) | (0°, 0°, 0°) |
| 7 | Horizontal rotation right | (0°, 0°, 0°) | (0°, 0°, 45°) |
| 8 | Horizontal return right | (0°, 0°, 45°) | (0°, 0°, 0°) |
| 9 | Horizontal rotation left | (0°, 0°, 0°) | (0°, 0°, −45°) |
| 10 | Horizontal return left | (0°, 0°, −45°) | (0°, 0°, 0°) |

The end points of each movement may vary from one patient to the next and/or from therapy session to the next. Alternative sequences of maneuvering steps are also possible.

Advantageously, the apparatus is arranged such that the angles ($\theta$, $\phi$, $\rho$) of the patient correspond to the angles of substantially pure roll, pitch and yaw of the manipulator 11. This facilitates controlling and/or programming the apparatus and may optimise the use of the range of motion available to the manipulator. Start positions and end positions of the head and thus of the support may also be defined for complex motions, depending on the size of the patient 3.

Figure 5:
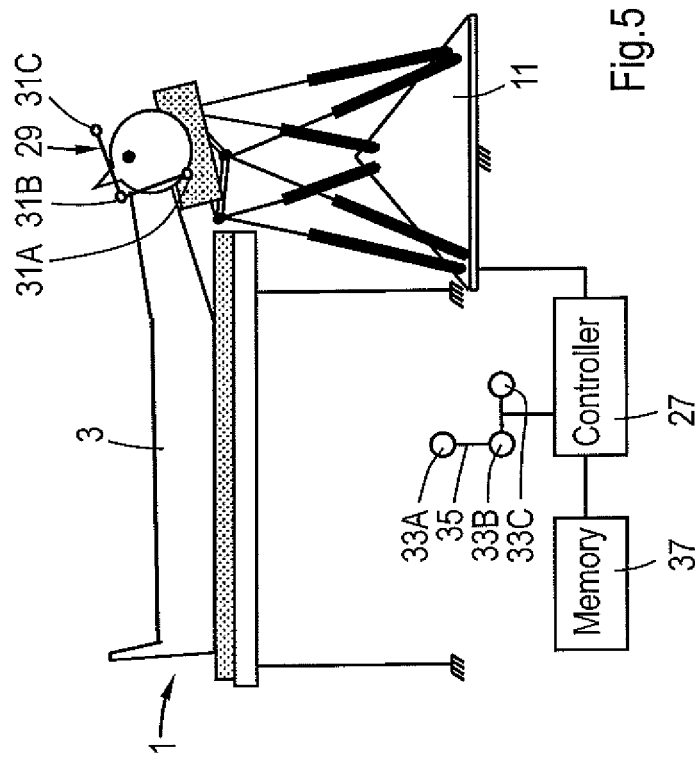
FIG. 5 shows an alternative embodiment of an apparatus for treating a head of a patient.

FIG. 5 shows a second embodiment of an apparatus 1. The apparatus 1 comprises a patient wearable object, here a headgear 29 (which can be in the form of a spectacles frame, a helmet, or a head band, for example) worn by the patient 3 and provided with three signal sources in the form of transmitters 31A-31C for emitting ultrasound pulses and radio pulses. The apparatus 1 further comprises three signal detectors in de the form of ultrasound detectors 33A-33C and at least one radio detector (not shown) for detecting the ultrasound pulses and radio pulses, respectively, of the transmitters 31A-31C. All detectors 33A-33C are connected to the controller. A radio detector may be included in an ultrasound detector. Each detector 33A-33C is attached to a frame 35, or optionally some other object such as a wall, the second support 9, etc. as long as it can detect the signals emitted by the transmitters 31A-31C. In particular in case of ultrasound signals or optical signals there should be a substantially clear and obstacle-free, "line of sight" between the sources 31A-31C and detectors 33A-33C to prevent possible deterioration or loss of the signal. The apparatus 1 further comprises a clock (not shown) and a memory 37 for storing data.

The transmitters 31A-31C are arranged to define a first plane through the transmitters 31A-31C. The detectors 33A-33C are arranged to define a second plane through the detectors 33A-33C.

In use, a first transmitter 31A generates a radio signal and an ultrasound signal. The signals may comprise one or more pulses or pulse trains, and possibly comprise information for identification of the transmitter 31A-31C. The radio signal is detected by the radio detector. The ultrasound signals are detected by each of the detectors 33A-33C and (the moment of) the detection is signalled to the controller 27. From the time of detection of the radio signal by the radio detector, the detectors 33A-33C and the controller 27 measure the time of arrival of the ultrasound signal on each detector 33A-33C to determine respective signal travelling times T(31A,33A), T(31A,33B) and T(31A,33C). Differences between the signal travelling times T(31A,33A), T(31A,33B) and T(31A,33C) as a consequence of different travelled distances allow determining the position of the signal source relative to the detectors. Determining all combinations of signal travelling times T(31A,33A), T(31A,33B) and T(31A,33C); T(31B,33A), T(31B,33B) and T(31B,33C); T(31C,33A), T(31C,33B) and T(31C,33C) allows determining the relative orientations of the first and second planes spanned by the transmitters 31A-31C and the detectors 33A-33C. This results in full determination from the determined relative positions of the spatial position and orientation of the headgear 29, and thus the patients head 5, and the frame 35 relative to each other.

Also or alternatively, the support 7 may be provided with transmitters. Providing the patient side (headgear 29 and/or support 7, etc.) with transmitters 31 and the controller side or remote side (frame 35, etc.) with detectors 33 facilitates processing the signals: the headgear 29 may comprise low power battery fed signal sources 31 for emitting wireless transferrable signals, whereas detectors 33 can be wired to and/or integrated with the controller 27.

To increase reliability of the measurements, it is preferred that ultrasound sources are arranged at mutual separations of about 15 cm or larger. A larger separation increases reliability of the triangulation since a constant absolute inaccuracy will lead to a smaller relative error with increasing separation. This also applies for ultrasound detectors.

Another way to determine (variations in) the orientation of the body part comprises the use of one or more gyroscopes 40 and/or one or more inclinometers 41 attached to the body part and/or the support. An inclinometer may detect (a variation in) an orientation with respect to gravity and/or to another reference system, e.g. a magnetic field, advantageously the magnetic field of the earth. One inclinometer may be used to detect (variations in) orientation in one plane, and may thus provide substantially the same information as two signal sources (or detectors) and three detectors (or sources, respectively).

Preferably, at least two inclinometers are used for detecting (a variation in) an orientation in two spatial directions at an angle to each other, preferably perpendicular to each other, which allows to determine a three-dimensional inclination of the monitored object (body part and/or support). A gyroscope facilitates monitoring a velocity and/or an acceleration, and in particular an angular velocity and/or acceleration, and allows determining an angle of rotation by integration of the measured angular velocity over time.

In an advantageous embodiment, two inclinometers are arranged substantially perpendicular to each other, and are configured to measure inclination angles versus the local horizon (local ground plane), e.g. pitch and roll angles, which may correspond to the sagittal flexion angle $\theta$ (pitch) the horizontal rotation angle $\phi$ (roll). Also, a gyroscope is arranged to measure substantially perpendicular to the measurement planes of the inclinometers to measure a yaw rotation angle ($\rho$), which may correspond to the coronal tilt angle. Magnetic inclinometers and gyroscopes may be integrated in one integrated circuit.

In a particularly advantageous embodiment of a therapeutic apparatus, the support is provided with two or three signal sources and/or detectors, respectively, and the headgear comprises at least one signal source or detector, respectively, and one or two inclinometers and one or more gyroscopes. The signal sources and/or detectors preferably comprise ultrasound sources and/or detectors as before. Thus, the position and orientation of the support may be determined reliably, size of the support being relatively unimportant and thus allowing separation of the signal sources and/or detectors of over 15 cm. Further, the position and/or displacement of the headgear may be determined from the source and/or detector and (changes in) its orientation from the inclinometers and gyroscope(s), which may be integrated in a small-volume device, e.g. a single integrated circuit.

Therapists generally use maneuvering a body part to be treated both for diagnostic and therapeutic purposes, possibly in combination within one trajectory.

Figure 6:
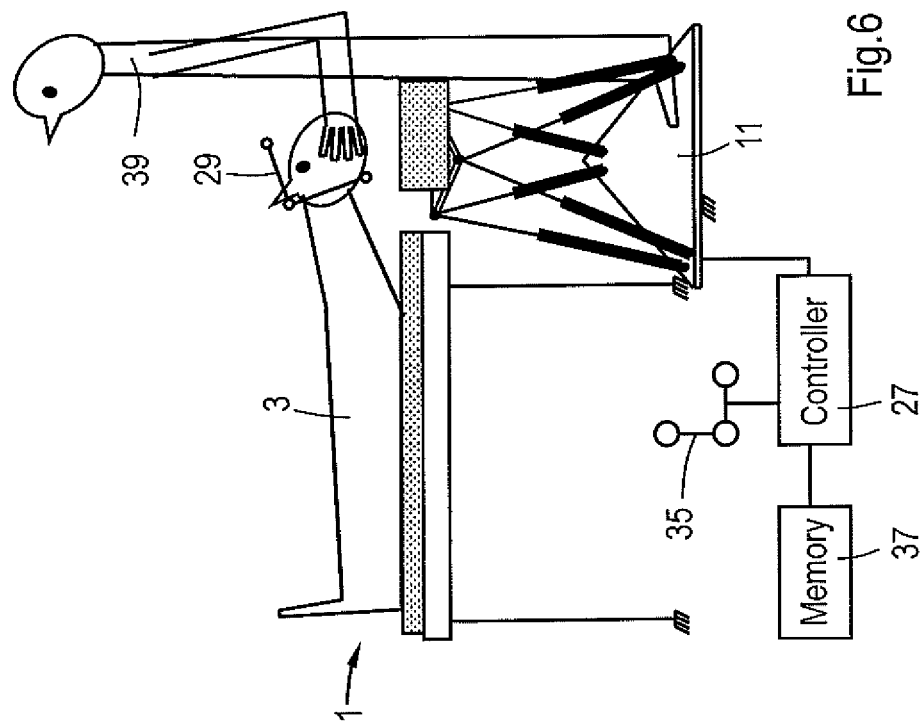

Referring now to FIGS. 6 and 7, in a typical therapeutic treatment session, the patient 3 is positioned on the first and/or second supports 7, 9 and the therapist 39 maneuvers the body part to be treated, here the head 5. During this, the therapist 39 may hold the body part 5 itself and/or the support 7 with the body part 5 attached to it. By directly holding the body part 5 the therapist 39 maneuvers and treats the patient 3 in regular fashion and at the same time receiving direct feedback from the patients body, facilitating diagnosis and monitoring treatment progression.

During treatment and/or diagnosis, the position and orientation of the body part 5 is determined repeatedly with the transmitters 31A-31C, detectors 33A-33C and the controller 27 and these data are stored with appropriate time stamps in the memory 37. Thus, the actual movements and trajectory of the body part 5 are recorded (and/or, in the appropriate case the movements and trajectory of the support 7).

When maneuvering a body part 5 provided with transmitters 31A-31C, the support 7 and/or the manipulator 11 may be at least partially lowered, moved away and/or removed altogether so as to provide freedom of posture and/or movement for the therapist 39.

For automated treatment by the apparatus 1, the manipulator 11 is placed in a desired position, possibly connected to a coupling on the treatment space floor and/or attached to the second support 9. Then, the body part 5 and the support 7 are placed in a desired position, e.g. by the therapist 39. The arrangement of (the actuators 19) of the manipulator 11 and the position of the support 7 are determined by the controller and the position and orientation of the body part 5 are determined with respect to (the frame 35 of) the apparatus, e.g. using signals from the signal sources 31 and detectors 33. Then, the treatment is administered by the apparatus 1 by operating one or more the actuators 19 under the control of the controller 27 to maneuver the support 7 in such a way that the body part 5 is maneuvered according to the trajectory defined by the therapist's maneuvering sequence.

The trajectory may be stored into or read from the memory 37 or another storage medium as software code portions for, when executed by the controller 27 operating at least part of the manipulator 11, e.g. at least one of the actuators 19 in a predetermined sequence of steps so as to maneuver the support 7 according to the desired maneuvering sequence for treating a body part 5 of a patient 3; this allows storage and transfer of the treatment to another treatment apparatus 1, to a patient file for further reference etc.

In the apparatus 1 of FIGS. 1, and 5-7 a Stewart platform 13 is arranged upright with the platform 17 supported by the actuators 19 above the base 15. In an alternative embodiment, see FIG. 8A the manipulator 11 comprises a Stewart platform 13 which is arranged substantially horizontal and the support 7 is suspended from the platform 17. This accommodates maneuvering the head 5 by a sitting therapist. However, the load on the Stewart platform 13 is less favourable than in the upright case and the manipulator 11 requires a stronger Stewart platform 13, which tend to be heavier, more expensive and possibly less accurate. This may also preclude the use of magnetic ball joints (which may have too little attractive force within acceptable financial and/or spatial constraints) but suitable tendon joints may readily be provided and used.

In the embodiment of FIG. 8A also a different design of a, plane, frame 35 with detectors 33 is shown. Further, a plane arrangement of transmitters 31 on the headgear 29 is visible.

FIG. 9 shows a cross-section view of a regular ball joint 41 comprising a ball 43 which is received in a matching receptacle 45. The ball 43 is connected or connectable to a further object with a threaded shaft 47. The ball 43 is held in position in the receptacle 45 by a ring 49.

FIGS. 10A and 10B indicate exemplary magnetic ball joints 51 for use as an improved hinge 21 in perspective view (FIG. 10A) and in cross-section view (FIG. 10B) comprising a ball 53 received in a matching receptacle 55. The ball 53 is connected or connectable to a further object, e.g. with a threaded shaft 57. The ball 53 is held in position in the receptacle 55 by a magnetic portion 59 attracting the ball 53.

From comparing FIGS. 9 and 10B it will be apparent that the magnetic ball joint 51 has a significantly larger freedom of movement between the receptacle 55 and the threaded shaft 57 than the regular ball joint 41 between the receptacle 45 and the threaded shaft 47.

FIGS. 11A-14 indicate different tendon joints 61 for use as an improved hinge 21, comprising a flexible tendon 63 attached to and interconnecting a first object 65, e.g. the base 15, and a second object 67, e.g. an actuator 19. The tendon 63 may be attached in any suitable way, e.g. with a clamping ring mount 69. Industrial rubber tendon joint tendons 63 may comprise a threaded nut for bolting the tendon to a further object. FIG. 11B illustrates that a sufficiently long and flexible tendon may—if also allowed by the shape of first and second objects 65, 67—easily bend to approx. 90° in any direction from a straight position, allowing a freedom of movement over a solid angle of substantially $2\pi$ steradians.

Figure 14:
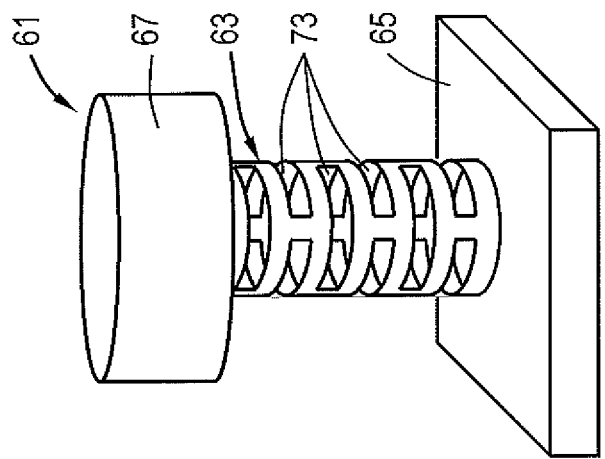
Figure 13:
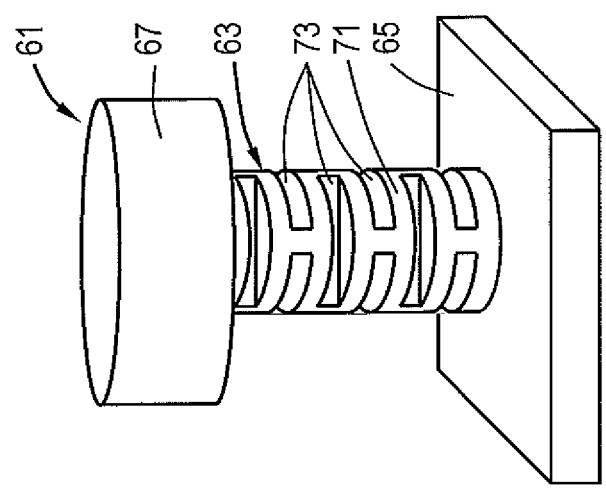
Figure 12:
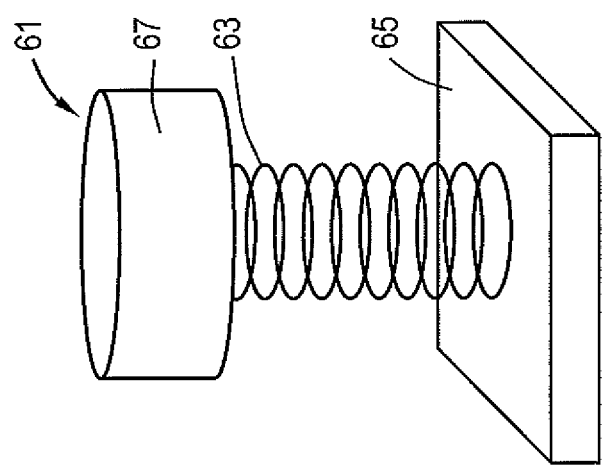

FIG. 12 schematically illustrates a resilient tendon joint 61 with a tendon 63 between two objects 65, 67 in the form of a helical coiled spring. FIG. 13 schematically illustrates a resilient tendon joint 61 with a tendon 63 formed by a rod 71 having periodic tangential or radial cuts 73 in different directions along the direction of extension of the rod 71. Here the cuts 73 are alternating in directions which are perpendicular to each other. FIG. 14 illustrates a tendon joint similar to FIG. 13 but with a tubular tendon 63 having cuts 73 through the wall of the tubular tendon 63. Yet another embodiment (not shown) comprises a tubular tendon having a harmonica-shaped tendon wall with oscillating diameter along the direction of extension of the tendon so as to impart flexibility and resiliency to the tube.

A tendon joint 21 fixed on one end to a base 15 or platform 17 and on another end to a spindle actuator 19 may exhibit some torsion, dependent on the construction and/or material of the tendon, but will sufficiently prevent rotation of the spindle actuator 19 with respect to the base 15 or platform 17 to obviate further measures for preventing undesired rotation of the spindle actuator 19 with respect to the base 15 or platform 17 and/or of the spindle 23 and the tube 25 with respect to each other.

The invention is not restricted to the above described embodiments which can be varied in a number of ways within the scope of the claims. For instance the apparatus may comprise one or more connectors, readers, writers and/or receivers for (connecting with) one or more storage media (not shown) and a memory, to provide and/or store data and/or a program for use by and/or programming of the controller.

The apparatus may comprise a user interface with which a user, e.g. a therapist, can adapt and/or program a maneuvering sequence and store it in the memory. E.g. by assembling stored maneuvering sequences to a desired trajectory or program a repetitive trajectory with increased movement amplitude (e.g. flexion angle, coronal translation, etc.) and/or velocity per repetition. Data from recorded treatment maneuvers and trajectories and/or software code portions for their execution by an apparatus 1 may be provided and/or sold on suitable storage media.

Different patient wearable objects may be provided apart or as a kit with a manipulator and/or a support, e.g. headgear of different sizes, so as to accommodate patient sizes, afflictions and/or user preferences, and/or for replacement.

The first support and at least part of a second support may be movably interconnected, as indicated in FIG. 7.

The method may comprise positioning and/or orienting the body part and/or an apparatus portion, e.g. the support, in one or more default positions and/or orientations, for reference purposes, increasing reliability of the determination and/or the maneuvering. This may comprise repeated returning to a starting position.

Elements and aspects discussed for or in relation with a particular embodiment may be suitably combined with elements and aspects of other embodiments, unless explicitly stated otherwise.

The invention claimed is:

1. An apparatus for treating a body part of a patient, comprising:
    a support configured to:
        support and hold the body part of the patient in a first position; and
        provide a free space for the body part to move without contacting the support in a second position;
    a manipulator connected to the support configured to support and maneuver the support wherein the manipulator comprises a parallel linkage device;
    a first portion and a second portion,
        wherein the first or the second portion comprises an object configured to be worn on the body part,
        wherein one of the first and second portions comprises a plurality of signal sources and the other one of the first and second portions comprises a plurality of detectors,
        wherein the plurality of signal sources are configured to emit signals and the plurality of detectors are configured to detect the signals from the plurality of signal sources in the second position, wherein the signals emitted from the plurality of signal sources and detected by the plurality of detectors being configured so as to provide a plurality of signal travelling times, thereby allowing determination of a position and an orientation of the body part independent of a position of the support; a controller configured to: determine a relative
    position of the first portion and the second portion using the plurality of signal travelling times and triangulation, and determine orientation of the first portion and the second portion based on the plurality of signal travelling times and triangulation, wherein the apparatus is configured to store information comprising a plurality of the determined relative positions and orientations of the first and second portions in a memory;
    read at least part of the information stored in the memory to define at least a first maneuvering sequence of the body part as a function of the information stored in the memory;
    control the apparatus to operate the manipulator to maneuver the support in the first position in such a way that the body part is supported by the support; and
    control the apparatus to operate the manipulator to maneuver the support to move the body part according to at least the first maneuvering sequence; and
    wherein the memory is configured to store the relative positions and orientations determined by the controller.

2. The apparatus according to claim 1, wherein the parallel linkage device comprises a Stewart-platform.

3. The apparatus according to claim 1, further comprising a second support configured to support a second body part of the patient.

4. The apparatus according to claim 1, wherein the plurality of signal sources are configured to comprise a first signal contemporarily emitted with a second signal, the first signal being a relatively slower signal than the second signal.

5. The apparatus according to claim 1, wherein the plurality of signal sources are configured to comprise a first signal contemporarily emitted with a second signal, the first signal including ultrasound waves and the second signal including electromagnetic radiation.

6. An apparatus for treating a body part of a patient, comprising:
    a support configured to:
        support and hold the body part of the patient in a first position; and
        provide a free space for the body part to move without contacting the support in a second position;
    a manipulator connected to the support configured to support and maneuver the support wherein the manipulator comprises a parallel linkage device;
    a first portion and a second portion,
        wherein the first or the second portion comprises an object configured to be worn on the body part,
        wherein one of the first and second portions comprises at least one of an inclinometer and a gyroscope, and
        wherein one of the first and second portions comprises:
            at least one signal source and the other one of the first and second portions comprises multiple detectors, or
            at least one detector and the other one of the first and second portions comprises multiple signal sources,
        wherein the at least one signal source and the multiple detectors, or the at least one detector and the multiple signal sources are configured to provide a plurality of signal travelling times in the second position, thereby allowing determination of a position and an orientation of the body part independent of a position of the support; a controller configured to: determine a relative
    position of the first portion and the second portion using the plurality of signal travelling times and triangulation, and determine orientation of the first portion and the second portion and based on signals from the at least one of the inclinometer and the gyroscope, wherein the apparatus is configured to store information comprising a plurality of the determined relative positions and orientations of the first and second portions in a memory;
    read at least part of the information stored in the memory, to define at least a first maneuvering sequence of the body part as a function of the information stored in the memory;
    control the apparatus to operate the manipulator to maneuver the support in the first position in such a way that the body part is supported by the support; and
    control the apparatus to operate the manipulator to maneuver the support to move the body part according to at least the first maneuvering sequence; and
    wherein the memory is configured to store the relative positions and orientations determined by the controller.

7. The apparatus according to claim 6, wherein the parallel linkage device comprises a Stewart-platform.

8. The apparatus according to claim 6, further comprising a second support configured to support a second body part of the patient.

9. The apparatus according to claim 6, wherein the signal sources are configured to comprise a first signal contemporarily emitted with a second signal, the first signal being a relatively slower signal than the second signal.

10. The apparatus according to claim 6, wherein the signal sources are configured to comprise a first signal contemporarily emitted with a second signal, the first signal including ultrasound waves and the second signal including electromagnetic radiation.

11. A method of operating a physiotherapy apparatus, wherein the apparatus comprises:
  a support configured to support and hold a body part of a patient in a first position, and provide a free space for the body part to move without contacting the support in a second position, and
  a first portion and a second portion,
    wherein the first or the second portion comprises an object that is wearable on the body part,
    wherein one of the first and second portions comprises a plurality of signal sources and the other one of the first and second portions comprises a plurality of detectors,
    wherein the plurality of signal sources are configured to emit signals and the plurality of detectors are configured to detect the signals from the plurality of signal sources in the second position, wherein the signals emitted from the plurality of signal sources and detected by the plurality of detectors being configured so as to provide a plurality of signal travelling times, thereby allowing determination of a position and an orientation of the body part independent of a position of the support, the method
  comprising:
    a) when the support is in the second position, obtaining the plurality of signal traveling times;
    b) determining a relative position and the orientation of the first and second portions based on the plurality of signal travelling times;
    c) storing the determined relative positions and orientations of the first and second portions in a memory;
    d) determining a maneuvering sequence of the body part based on the stored relative positions and orientations;
    e) moving the support of the apparatus from the second position to the first position to support and hold the body part; and
    f) after the support is moved to the first position, controlling a manipulator of the apparatus to maneuver the support of the apparatus to move the body part according to the maneuvering sequence.

12. The method according to claim 11, wherein moving the support comprises moving the support in three mutually perpendicular directions including X, Y, and Z and three degrees of rotation including roll, pitch, and yaw.

13. The method according to claim 11, further comprising using a second support configured to support a second body part of the patient.

14. The method according to claim 11, further comprising the plurality of signal sources emitting a first signal contemporarily emitted with a second signal, the first signal being a relatively slower signal than the second signal.

15. The method according to claim 11, further comprising the plurality of signal sources emitting a first signal contemporarily emitted with a second signal, the first signal including ultrasound waves and the second signal including electromagnetic radiation.

16. A method of operating a physiotherapy apparatus, wherein the apparatus comprises:
  a support configured to support and hold a body part of a patient in a first position, and provide a free space for the body part to move without contacting the support in a second position, and
  a first portion and a second portion,
    wherein the first or the second portion comprises an object that is wearable on the body part,
    wherein one of the first and second portions comprises:
      at least one signal source and the other one of the first and second portions comprises multiple detectors, or
      at least one detector and the other one of the first and second portions comprises multiple signal sources,
    wherein the at least one signal source and the multiple detectors, or the at least one detector and the multiple signal sources are configured to provide a plurality of signal travelling times in the second position, thereby allowing determination of a position and an orientation of the body part independent of a position of the support, the method
  comprising:
    a) when the support is in the second position, obtaining the plurality of signal traveling times;
    b) determining a relative position and the orientation of the first and second portions based on:
      the plurality of signal travelling times, and
      measurement data of at least one of orientation and acceleration;
    c) storing the determined relative positions and orientations of the first and second portions in a memory;
    d) determining a maneuvering sequence of the body part based on the stored relative positions and orientations;
    e) moving the support of the apparatus from the second position to the first position to support and hold the body part; and
    f) after the support is moved to the first position, controlling a manipulator of the apparatus to maneuver the support of the apparatus to move the body part according to the maneuvering sequence.

17. The method according to claim 16, wherein moving the support comprises moving the support in three mutually perpendicular directions including X, Y, and Z and three degrees of rotation including roll, pitch, and yaw.

18. The method according to claim 16, further comprising using a second support configured to support a second body part of the patient.

19. The method according to claim 16, further comprising the signal sources emitting a first signal contemporarily emitted with a second signal, the first signal being a relatively slower signal than the second signal.

20. The method according to claim 16, further comprising the signal sources emitting a first signal contemporarily emitted with a second signal, the first signal including ultrasound waves and the second signal including electromagnetic radiation.

* * * * *